US009181148B2

(12) United States Patent
Katikaneni et al.

(10) Patent No.: US 9,181,148 B2
(45) Date of Patent: Nov. 10, 2015

(54) NI/CGO AND NI-RU/CGO BASED PRE-REFORMING CATALYSTS FORMULATION FOR METHANE RICH GAS PRODUCTION FROM DIESEL PROCESSING FOR FUEL CELL APPLICATIONS

(71) Applicants: Saudi Arabian Oil Company, Dhahran (SA); Korea Advanced Institute of Science and Technology, Yuseong-gu, Daejeon (KR)

(72) Inventors: Sai P. Katikaneni, Dhahran (SA); Joongmyeon Bae, Yuseong-gu (KR); Sangho Lee, Yuseong-gu (KR)

(73) Assignees: Saudi Arabian Oil Company, Dhahran (SA); Korea Advanced Institute of Science and Technology, Yuseong-Gu Daejeon Republic (KR)

( * ) Notice: Subject to any disclaimer, the term of this patent is extended or adjusted under 35 U.S.C. 154(b) by 110 days.

(21) Appl. No.: 13/900,042

(22) Filed: May 22, 2013

(65) Prior Publication Data

US 2014/0350318 A1     Nov. 27, 2014

(51) Int. Cl.
*B01J 23/10*        (2006.01)
*B01J 23/83*        (2006.01)
(Continued)

(52) U.S. Cl.
CPC ............... *C07C 4/06* (2013.01); *B01J 23/755* (2013.01); *B01J 23/76* (2013.01); *B01J 23/83* (2013.01); *B01J 23/892* (2013.01); *B01J 23/894* (2013.01); *B01J 35/026* (2013.01); *B01J 37/18* (2013.01); *B01J 38/06* (2013.01); *B01J 38/10* (2013.01); *B01J 37/031* (2013.01); *B01J 2523/00* (2013.01);

(Continued)

(58) Field of Classification Search
CPC .......... B01J 23/10; B01J 23/755; B01J 23/83; B01J 37/00; B01J 37/08; B01J 38/06; B01J 2523/3712; B01J 2523/375; B01J 2523/847; C07C 4/06
USPC ................... 502/20, 22, 34, 53, 302, 304, 337
See application file for complete search history.

(56) References Cited

U.S. PATENT DOCUMENTS 6,110,861  A    8/2000  Krumpelt et al.
6,238,816  B1   5/2001  Cable et al.
(Continued)

FOREIGN PATENT DOCUMENTS

EP    2012381 A1 *  1/2009  .............. H01M 4/86
EP    2031675 A1 *  3/2009  .............. H01M 4/04

OTHER PUBLICATIONS

"Effect of nickel nano-particle sintering on methane reforming activity of Ni-CGO cermet anodes for internal steam reforming SOFCs," D. Hari Prasad et al. Applied Catalysis B: Environmental 101 (2011), pp. 531-539.*

(Continued)

*Primary Examiner* — Patricia L Hailey
(74) *Attorney, Agent, or Firm* — Bracewell & Giuliani LLP; Constance Gall Rhebergen

(57) ABSTRACT

In one aspect, the invention provides a catalyst for converting diesel type liquid hydrocarbons to methane rich gas. The catalyst includes a nickel component, a cerium oxide component, and gadolinium oxide component. The catalysts provide high conversion, selectivity, and stability compare to the state of the art commercial catalysts. The catalyst compositions can improve the overall fuel cell efficiency for both mobile and stationary fuel cell applications.

18 Claims, 20 Drawing Sheets

TEM images of Ni/CGO

(51) Int. Cl.

| | | |
|---|---|---|
| B01J 37/00 | (2006.01) | |
| B01J 37/08 | (2006.01) | |
| B01J 38/06 | (2006.01) | |
| C07C 4/06 | (2006.01) | |
| B01J 23/76 | (2006.01) | |
| B01J 37/18 | (2006.01) | |
| B01J 38/10 | (2006.01) | |
| B01J 23/755 | (2006.01) | |
| B01J 23/89 | (2006.01) | |
| B01J 35/02 | (2006.01) | |
| B01J 37/03 | (2006.01) | |
| H01M 8/06 | (2006.01) | |
| H01M 8/12 | (2006.01) | |

(52) U.S. Cl.
 CPC ..... *H01M 8/0618* (2013.01); *H01M 2008/1293* (2013.01); *Y02E 60/525* (2013.01)

(56) References Cited

U.S. PATENT DOCUMENTS

| 6,458,741 | B1* | 10/2002 | Roark et al. ............... 502/303 |
|---|---|---|---|
| 6,749,829 | B2 | 6/2004 | Briscoe |
| 7,067,453 | B1 | 6/2006 | Ming et al. |
| 7,168,265 | B2 | 1/2007 | Briscoe et al. |
| 7,452,619 | B2 | 11/2008 | Ahmed |
| 7,473,466 | B1 | 1/2009 | Muradov |
| 7,572,429 | B1 | 8/2009 | Neylon et al. |
| 7,829,602 | B2 | 11/2010 | Litt et al. |
| 7,901,565 | B2 | 3/2011 | Giroux et al. |
| 8,076,121 | B2 | 12/2011 | O'Rear |
| 8,123,826 | B2 | 2/2012 | Pham |
| 2004/0245086 | A1 | 12/2004 | Steynberg et al. |
| 2008/0003461 | A1 | 1/2008 | Chellappa |
| 2008/0003466 | A1 | 1/2008 | Stevens et al. |
| 2008/0057359 | A1 | 3/2008 | Venkataraman et al. |
| 2008/0262110 | A1 | 10/2008 | Lomax et al. |
| 2009/0155644 | A1 | 6/2009 | Cui et al. |
| 2009/0305090 | A1 | 12/2009 | Chuang |
| 2010/0183490 | A1 | 7/2010 | Hoke et al. |
| 2011/0024687 | A1 | 2/2011 | White et al. |
| 2011/0065017 | A1 | 3/2011 | Ha et al. |
| 2012/0003565 | A1* | 1/2012 | Son et al. ............... 429/496 |
| 2012/0015266 | A1 | 1/2012 | Melo Faus et al. |
| 2012/0024757 | A1* | 2/2012 | Xia et al. ............... 208/177 |
| 2012/0070367 | A1 | 3/2012 | Bittencourt |

OTHER PUBLICATIONS

"Single step synthesis of nano-sized NiO—Ce0.75Zr0.25O2 composite powders by glycine nitrate process," D. Hari Prasad et al. Materials Letters 62 (2008), pp. 587-590.*

"Autothermal reforming study of diesel for fuel cell application," Inyong Kang et al. Journal of Power Sources 159 (2006), pp. 1283-1290.*

"Ni—Ce0.9Gd0.1O1.95 anode for GDC electrolyte-based low-temperature SOFCs", Shaowu Zha et al. Solid State Ionics 166 (2004), pp. 241-250.*

"The micro-reactor testing of catalysts and fuel delivery apparatuses for diesel authothermal reforming," Inyong Kang et al. Catalysis Today 136 (2008), pp. 249-257.*

Fridriksson, H., Study on Catalytic Reactions in Solid Oxide Fuel Cells with Comparison to Gas Phase Reactions in Internal Combustion Engines, 2008 TFRFO5 Fuel Cell Technology, Dec. 3, 2009, Lund, Sweden.

Song, C., Fuel Processing for Low-Temperature and High-Temperature Fuel Cells Challenges, and Opportunities for Sustainable Development in the 21st Century, Catalysis Today, Jan. 1, 2002, pp. 17-49, vol. 77, www.elsevier.com/locate/cattod, Elsevier Science B.V.

International Search Report and Written Opinion for related PCT Application PCT/US2014/039132, Oct. 9, 2014.

Prasad et al., Internal Steam Reforming of Methane over Ni-GDC Anode Particles Prepared by Glycine-nitrate-process for SOFC Applications, The 10th Asian Hydrogen Energy Conference "AHEC2009", Daegu, Korea, 2009, pp. 217-233.

* cited by examiner

TEM images of Ni/CGO

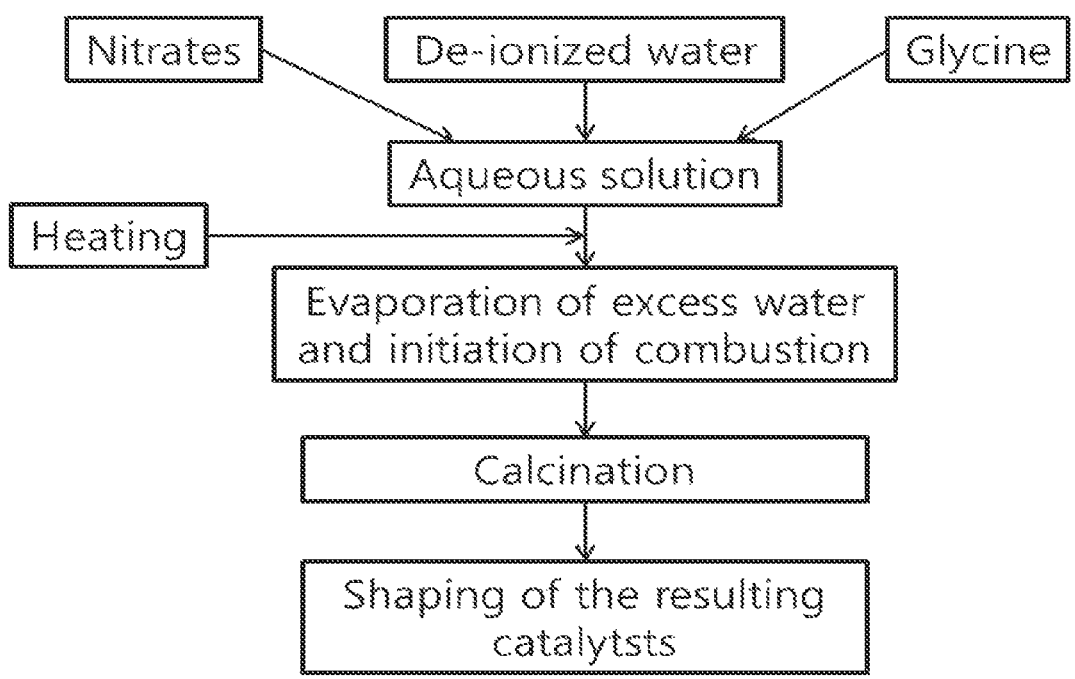
Fig. 2 Schematic flowcharts of preparation method

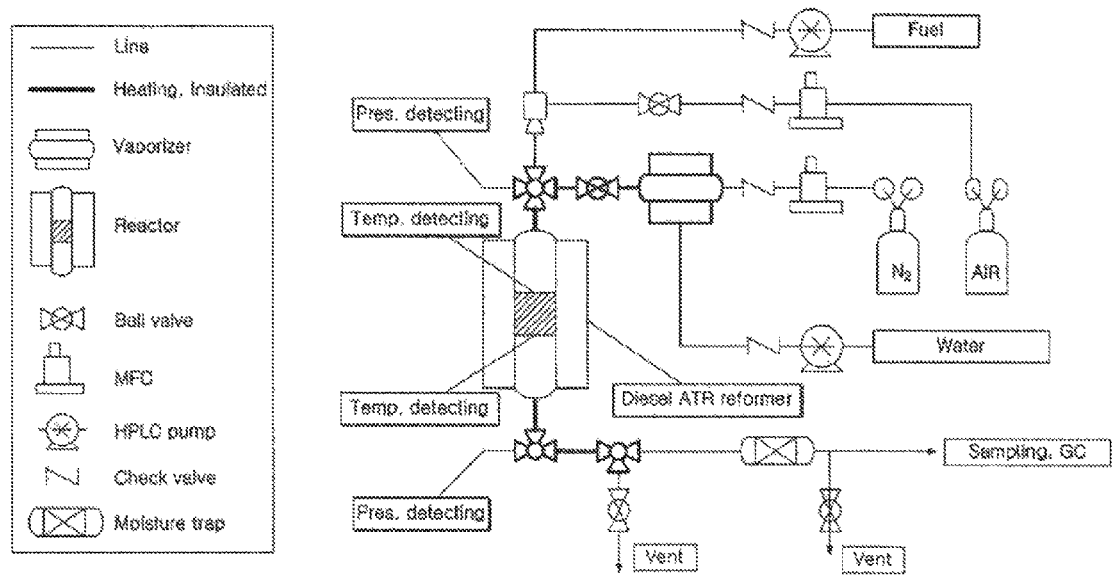
Fig. 3 Schematic diagram of experimental setup for catalytic activity (a)

Fuel conversion and $CH_4$ production over mono-metallic catalysts (b)

Fuel conversion and CH₄ production over mono-metallic catalysts

Fuel conversion over Ru/CGO (3.0 wt.%)

(a)

Fuel conversion and $CH_4$ production over bi metallic catalysts (b)

Fuel conversion and CH$_4$ production over bi metallic catalysts

Amount of coke formation over CGO and $Al_2O_3$

Amount of coke formation over various Ni content of Ni/CGO

Activity vs Ni loading

Stability test of Ni/CGO with 0.5 wt.% of precious metals

Stability test of Ni/CGO with various wt.% of Ru

XRD patterns of Ni/CGO and commercial CGO

Commercial diesel pre-reforming over Ni/CGO (20.0 wt. %) prepared by GNP and incipient wetness impregntion (IWI)

TPR profiles of Ni/CGO (20.0 wt. %) prepared by GNP and IWI

Accelerated degradation tests of various Ni/CGO catalysts

Accelerated degradation tests of Ni-Me/CGO (Me: Rh. Pt and Ru) catalysts

Accelerated degradation tests of Ni-Ru/CGO catalysts with various Ru wt.%

Long-term stability of 19.5 wt.% of Ni+0.5 wt.% Ru/CGO

NI/CGO AND NI-RU/CGO BASED PRE-REFORMING CATALYSTS FORMULATION FOR METHANE RICH GAS PRODUCTION FROM DIESEL PROCESSING FOR FUEL CELL APPLICATIONS

FIELD OF THE INVENTION

Generally, this invention relates to new catalyst formulations to convert diesel type liquid hydrocarbons to methane rich gas that results in increased fuel cell efficiency. The catalysts provide high conversion, selectivity, and stability compared to the state of the art commercial catalysts. The catalyst compositions improves the overall fuel cell efficiency for both mobile and stationary fuel cell applications.

BACKGROUND OF THE INVENTION

The present invention relates to diesel pre-reforming catalysts for use with diesel to create a methane-rich syngas for fuel cells. Pre-reforming partially completes a steam reforming reaction at a much lower temperature than steam reforming and using a highly active catalyst. Pre-reforming processes convert heavy hydrocarbons into methane-rich syngas. Catalytic pre-reforming typically reforms feedstocks from natural gas up to naphthas. Diesel, however, is an attractive hydrocarbon fuel for fuel cells. Diesel has the advantages of high energy density, well-constructed infrastructure, and safety. While natural gas, liquefied petroleum gas, and the like are converted through pre-reforming relatively easily, diesel cannot be easily pre-reformed. Diesel is a liquid fuel that is a complex mixture of hydrocarbons, including saturates, olefins and aromatics. The wide boiling range of the components creates complexities relative to mixing, evaporation, methane generation, catalyst fouling and fuel input steps that are not at issue with lower weight hydrocarbons.

Solid oxide fuel cells ("SOFC") use methane and hydrogen, as well as carbon monoxide. SOFC systems are less complex than other fuel cells because they have fuel flexibility. SOFC are capable of internally reforming methane. The internal reforming of methane also suppresses temperature increases in a SOFC stack. Heat generated from SOFC is accumulated in the SOFC stack. Unless the heat is properly released, the temperature of upper cells increases. This can lead to the failures of SOFC, as well as failures of sealant and interconnect materials. Internal reforming of methane is one manner of addressing the heat issue because the reaction by which methane is reformed is endothermic.

Diesel pre-reforming has historically experienced problems with coke formation and low operating temperature activity reduction. Diesel reforming catalysts are readily deactivated by coke formation. These types of heavy hydrocarbons are more prone to coke formation than light hydrocarbons. Coke formation is the main deactivation mechanism of these catalysts. In addition, pre-reforming is preferably operated at lower temperature than other reforming methods in order to encourage methane production. Pre-reforming is generally operated under 500° C. because the presence of methane is favorable at these temperature ranges. However, catalytic activity is typically proportional to the operating temperature. Therefore, the lower the operating temperature, the lower the activity of the catalyst. It would be advantageous to develop a catalyst with high tolerance to coke formation and high activity under 500° C. as a diesel pre-reforming catalyst.

Commercial catalysts are available for naphtha pre-reforming processes. However, the these commercial catalysts are not very useful or effective when used in a diesel pre-reforming processes. Diesel is more prone to coke formation than naphtha. Therefore, catalytic activities are degraded rapidly in diesel pre-reforming conditions.

Catalyst development is required for diesel pre-reforming processes. In a pre-reforming process, diesel is reformed into syngas before being fed to SOFC systems. Pre-reforming is operated without an oxygen feed and at lower than 500° C. Therefore, pre-reforming has higher efficiency than other reforming methods. However, a highly active catalyst is required for diesel pre-reforming because of characteristic of diesel and low operation temperature. No commercial catalysts are currently available for diesel pre-reforming. Additionally, no commercial catalysts are available to process diesel type liquid hydrocarbons to methane rich gas that can provide high fuel conversion, selectivity, and stability.

SUMMARY

Generally, this invention relates to new catalyst formulations to convert diesel type liquid hydrocarbons to methane rich gas that can result in increased fuel cell efficiency. The catalysts provide high conversion, selectivity, and stability compared to the state of the art commercial catalysts. The catalysts can improve the overall fuel cell efficiency for both mobile and stationary fuel cell applications.

In one aspect, the invention provides a catalyst for converting diesel type liquid hydrocarbons to methane rich gas. The catalyst includes a nickel component, a cerium oxide component, and gadolinium oxide component. The catalyst is operable to convert diesel type liquid hydrocarbons to methane rich gas.

In another aspect, the invention provides a catalyst for converting diesel type liquid hydrocarbons to methane rich gas. The catalyst includes a nickel component, a cerium oxide component, and gadolinium oxide component. The catalyst is resistant to the formation of coke on the catalyst during use of the catalyst.

In another aspect, the invention provides a method of preparing the catalyst for converting diesel type liquid hydrocarbons to methane rich gas using a glycine nitrate process. The process includes adding stoichiometric amounts of $Ce(NO_3)_3 \cdot 6H_2O$, $Gd(NO_3)_3 \cdot 6H_2O$ and $Ni(NO_3)_2 \cdot 6H_2O$ to de-ionized water to create a dissolved solution. Glycine is added to the dissolved solution to create a glycine-dissolved solution. The glycine-dissolved solution is heated such that excess water is evaporated, combustion is initiated, and a catalyst powder is produced. The catalyst powder is then calcined in air at 800° C. for 4 hours.

In another aspect, the invention provides a method of activating the catalyst by reducing the catalyst with hydrogen and nitrogen at about 500° C. for about 4 hours, such that the catalyst is activated.

In another aspect, the invention provides a method of regenerating the catalyst by treating a catalyst that has been used for converting diesel type liquid hydrocarbons to methane rich gas with a treatment of water, hydrogen, and nitrogen at atmospheric pressure, and about 500° C., for a sufficient amount of time to remove coke formation on the catalyst. The temperature of the regeneration process is dependent on the amount of coke formation. In some embodiments, the catalyst is treated at about 500° C. during the regeneration process. In further embodiments, the catalyst is treated from about 500° C. to about 800° C. during the regeneration process.

In another aspect, the invention provides a method of using the catalyst wherein diesel type liquid hydrocarbons are applied to the catalyst and a methane rich gas is produced.

The present invention has potential positive environmental impact. Global carbon dioxide emissions from fossil sources are significant. Reduction of global carbon dioxide emissions will reduce impacts on climate change. The combination of an on-board vehicle reformer and SOFC is expected to substantially lower greenhouse gas emissions because it has increased efficiency and will reduce fuel consumption.

BRIEF DESCRIPTION OF THE DRAWINGS

FIG. 2 shows a schematic flow chart of an embodiment of a preparation method of catalysts.

FIG. 3 shows the schematic of an experimental set-up.

DETAILED DESCRIPTION OF THE INVENTION

Figure 1:
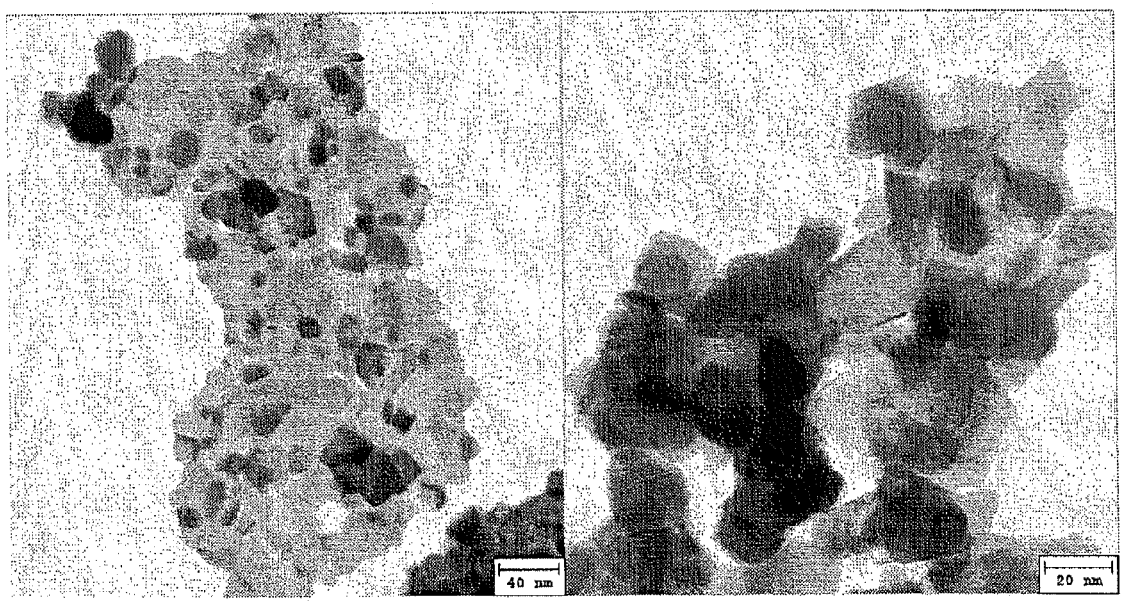
FIG. 1 shows transmission electron microscopy (TEM) images of exemplary catalyst particles formed according to an embodiment of the invention.

Generally, this invention relates to new catalyst formulations to convert diesel type liquid hydrocarbons to methane rich gas that can result in increased fuel cell efficiency. The catalysts provide high conversion, selectivity, and stability compared to the state of the art commercial catalysts. The catalyst compositions can improve the overall fuel cell efficiency for both mobile and stationary fuel cell applications. Hereinafter, the composition, the preparation method, the activation process, the regeneration process, and the use of diesel pre-reforming catalysts presented in the invention will be described in detail.

In one aspect, the invention provides a catalyst for converting diesel type liquid hydrocarbons to methane rich gas. Diesel type liquid hydrocarbons typically include a mixture of heavy hydrocarbons whose carbon number is in the range from 12 to 24. The catalyst includes a nickel component, a cerium oxide component, and gadolinium oxide component. The catalyst is operable to convert diesel type liquid hydrocarbons to methane rich gas.

In another aspect, the invention provides a catalyst for converting diesel type liquid hydrocarbons to methane rich gas. The catalyst includes a nickel component, a cerium oxide component, and gadolinium oxide component. The catalyst is resistant to the formation of coke on the catalyst during use of the catalyst.

In some embodiments, the nickel component is present at about 20% wt., the cerium oxide component is present at about 70% wt., and the gadolinium oxide component is present at about 10% wt. Surprisingly, it has been discovered that there is an optimum loading of nickel in the these catalyst compositions. It has been discovered that 20% wt. of Ni loading more effectively suppresses detrimental coke formation than higher Ni loading in the catalyst compositions.

In some embodiments, the catalyst further includes ruthenium. In further embodiments, when the catalyst includes ruthenium, the nickel component is present at about 19.5% wt., the cerium oxide component is present at about 70% wt., the gadolinium oxide component is present at about 10% wt., and the ruthenium component is present at about 0.5% wt. Surprisingly, a small addition of ruthenium improves the stability of these catalyst compositions. While nickel is widely used for catalytic processes because it has high catalytic activity and is inexpensive, nickel is vulnerable to coke formation compared to precious metals such as rhodium, platinum and ruthenium.

The nickel component is an active metal of the catalyst. The cerium and gadolinium components (collectively "CGO" or "Gd doped $CeO_2$") function as the catalyst support. The CGO is effective to improve the tolerance of the catalyst composition to coke formation. Without wishing to be bound by theory, it is believed that CGO suppresses coke formation on metals because CGO is an ionic conductive material. In some embodiments, the CGO has a high ionic conductivity. Thus, in further preferred embodiments, the catalyst is resistant to the formation of coke on the catalyst during use of the catalyst.

In another aspect, the invention provides a method of preparing the catalyst for converting diesel type liquid hydrocarbons to methane rich gas using a glycine nitrate process ("GNP"). The process includes adding stoichiometric amounts of $Ce(NO_3)_3.6H_2O$, $Gd(NO_3)_3.6H_2O$ and $Ni(NO_3)_2.6H_2O$ to de-ionized water to create a dissolved solution. Glycine is added to the dissolved solution to create a glycine-dissolved solution. The glycine-dissolved solution is heated such that excess water is evaporated, combustion is initiated, and a catalyst powder is produced. The catalyst powder is calcined in air at 800° C. for 4 hours. The resulting powder after the combustion is calcinated in order to stabilize the active metal and form the phase of CGO ($Ce_{0.9}Gd_{0.1}O_{2-x}$). To effectively suppress coke formation, the phase of CGO should be formed during the calcination.

Glycine is used as a fuel for glycine nitrate process, and after the combustion, the glycine should be combusted. Therefore, the amount and purity of glycine are less important than other elements. However, in some embodiments a 1:1.5 nitrate:glycine molar ratio is used for the process. In some embodiments a ≥99% purity glycine is used. In further embodiments, the molar ratio of glycine to $NO_3$ of the glycine-dissolved solution is about 1.4. In further embodiments, the molar ratio of glycine to $NO_3$ of the glycine-dissolved solution is about 1.6.

In some embodiments, the catalyst powder is shaped into a form for use in converting diesel type liquid hydrocarbons to methane rich gas. In further embodiments, the form is catalyst pellets. A person of skill in the art will understand the various forms in to which the catalysts could be shaped, and will understand how to select the best form for a given reactor and process. In some embodiments, the catalyst powder is pelletized using a hydraulic press. A person of skill in the art will understand the various other methods that can be used to shape catalysts.

In further embodiments, the catalyst powder has particles in the size range of 10 nm to 20 nm. In some embodiments, the particles are a combination of sizes within this range. In other embodiments, the particles form a large cluster. This large cluster is shown in FIG. 1 which is TEM (Transmission Electron Microscope) images of an exemplary prepared catalyst.

In some embodiments, the calcining the catalyst powder step includes increasing the temperature to about 800° C. over a period of about 4 hours, and then maintaining the temperature at about 800° C. for about 4 hours. FIG. 2 shows an exemplary schematic flowchart illustrating the preparation method of catalyst compositions according to certain embodiments of the present invention.

In another aspect, the invention provides a method of activating the catalyst by reducing the catalyst with hydrogen and nitrogen at about 500° C. for about 4 hours, such that the catalyst is activated. In some embodiments, the hydrogen is about 30% wt. In other embodiments, the nitrogen is about 70% wt. Pretreatment, or activation, of the catalyst compositions is necessary as nickel converts to a non-active form of nickel oxide during the preparation of the catalyst compositions.

In another aspect, the invention provides a method of regenerating the catalyst by treating a catalyst that has been used for converting diesel type liquid hydrocarbons to methane rich gas with a treatment of water, hydrogen, and nitrogen at atmospheric pressure, and about 500° C. for a sufficient amount of time to remove coke formation on the catalyst. The temperature of the regeneration process is dependent on the amount of coke formation. In some embodiments, the catalyst is treated at about 500° C. during the regeneration process. In further embodiments, the catalyst is treated from about 500° C. to about 800° C. during the regeneration process. In general, a higher regeneration temperature can be used for treating more severe coke formation. For instance, with severe coke formation, a temperature of 800° C. can be used during the regeneration process. In some embodiments, the hydrogen is about 30% wt. In some embodiments, the nitrogen is about 45% wt. In some embodiments, the water is about 45% wt. In some embodiments, about 90% of the coke formed on the catalyst during use is removed during regeneration. In some embodiments, about 91% of the coke formed on the catalyst during use is removed during regeneration. In some embodiments, about 92% of the coke formed on the catalyst during use is removed during regeneration. In some embodiments, about 93% of the coke formed on the catalyst during use is removed during regeneration. In some embodiments, about 94% of the coke formed on the catalyst during use is removed during regeneration. In some embodiments, about 95% of the coke formed on the catalyst during use is removed during regeneration. In some embodiments, about 96% of the coke formed on the catalyst during use is removed during regeneration. In some embodiments, about 97% of the coke formed on the catalyst during use is removed during regeneration. In some embodiments, about 98% of the coke formed on the catalyst during use is removed during regeneration. In some embodiments, about 99% of the coke formed on the catalyst during use is removed during regeneration. In some embodiments, about 100% of the coke formed on the catalyst during use is removed during regeneration.

In another aspect, the invention provides a method of using the catalyst wherein diesel type liquid hydrocarbons are applied to the catalyst and a methane rich gas is produced. In some embodiments, the diesel type liquid hydrocarbons are converted to methane rich gas at a rate of about 10% or greater. In some embodiments, the diesel type liquid hydrocarbons are converted to methane rich gas at a rate of about 11% or greater. In some embodiments, the diesel type liquid hydrocarbons are converted to methane rich gas at a rate of about 12% or greater. In some embodiments, the diesel type liquid hydrocarbons are converted to methane rich gas at a rate of about 13% or greater.

In preferred embodiments, the catalysts have high catalytic activity and stability for diesel pre-reforming to obtain high efficiency and heat balance of a solid oxide fuel cell (SOFC) system.

In preferred embodiments, the catalysts provide high conversion, selectivity, and stability compared to the state of the art commercial catalysts. In some embodiments, the catalyst compositions can improve the overall fuel cell efficiency for both mobile and stationary fuel cell applications.

EXAMPLES

Activity tests and analysis of spent catalysts were conducted to design and optimize the catalyst compositions. Activity tests were used to compare the activity and stability of various catalyst compositions. The spent catalysts were then analyzed by temperature programmed oxidation to measure coke formation.

GNP-CGO catalyst formulations for all of the Examples were prepared as follows. Nickel/CGO catalysts were prepared by adding $Ce(NO_3)_3 \cdot 6H_2O$, $Gd(NO_3)_3 \cdot 6H_2O$, and $Ni(NO_3)_2 \cdot 6H_2O$ to de-ionized water to create a dissolved solution. The amount of each nitrate was stoichiometrically calculated. For example, to make 10% Ni/CGO catalyst, molar ratio of three components is $Ce(NO_3)_3 \cdot 6H_2O:Gd(NO_3)_3 \cdot 6H_2O:Ni(NO_3)_2 \cdot 6H_2O = 0.9:0.1:0.3290$. For 20% Ni/CGO catalyst, the molar ratio of $Ni(NO_3)_2 \cdot 6H_2O$ was changed to 0.7403 and so on. Glycine was added to the dissolved solution to create a glycine-dissolved solution. A 1:1.5 nitrate:glycine molar ratio is used. The glycine-dissolved solution was heated such that excess water was evaporated, combustion was initiated, and a catalyst powder was produced. About 2 hours were needed for vaporization of excess water, and spontaneous combustion began at approximately 180° C. During the combustion, internal temperature suddenly rose to above 1000° C. The combustion was completed in a few minutes. The catalyst powder was shaped into a pellet. The catalyst powder was then calcined in air increasing the temperature to about 800° C. over a period of about 4 hours, and then maintaining the temperature at about 800° C. for 4 hours. After the calcination, the calcined catalyst was ground uniformly with mortar and then shaped again into the pellet. The catalyst particles having 250 to 500 μm particle size were selected with sieves.

Nickel/Rhodinium/CGO catalysts, Nickel/Platinum/CGO catalysts, Ruthenium/CGO catalysts, Rhodium/CGO catalysts, Platinum/CGO catalysts, and Nickel/Ruthenium/CGO catalysts were prepared by a similar method as the GNP-CGO catalyst formulations. For example, the Nickel/Ruthenium/CGO catalysts were prepared by adding $Ce(NO_3)_3 \cdot 6H_2O$, $Gd(NO_3)_3 \cdot 6H_2O$, $Ni(NO_3)_2 \cdot 6H_2O$, and $Ru(NO)(NO_3)_3$ to de-ionized water to create a dissolved solution. The amount of each nitrate was stoichiometrically calculated. For example, to make 19.5% Ni-0.5% Ru/CGO catalyst, the molar ratio of four components is $Ce(NO_3)_3 \cdot 6H_2O:Gd(NO_3)_3 \cdot 6H_2O:Ni(NO_3)_2 \cdot 6H_2O:Ru(NO)(NO_3)_3 = 0.9:0.1:0.7218:0.01075$. Glycine was added to the dissolved solution to create a glycine-dissolved solution. A 1:1.5 nitrate:glycine molar ratio was used. The glycine-dissolved solution was heated about 2 hours to vaporize excess water, and spontaneous combustion began at approximately 180° C. During the combustion, the internal temperature suddenly rose to above 1000° C. The combustion was completed in a few minutes and the catalyst power was produced. The catalyst powder was shaped into a pellet and then calcined in air increasing the temperature to 800° C. over a period of about 4 hours, then maintaining the temperature at about 800° C. for 4 hours. After the calcination, calcined catalyst was ground uniformly with mortar and then shaped again into the pellet. The catalyst particles having 250 to 500 µm particle size were selected with sieves.

Incipient wetness impregnation (IWI) Nickel/CGO catalysts were prepared as follows. Gadolinium doped ceria (CGO) from PRAXAIR was dried at 130° C. for 4 hours. Dried CGO was weighted and deionized water was absorbed into dried CGO. After the absorption, the CGO was weighted again to calculate the ratio of absorbed water by porous structure of CGO. A nickel nitrate solution was prepared with stoichiometric amount of nickel components, and the solution was absorbed into dried CGO. Then, the nickel-containing CGO catalyst was dried at 120° C. for 4 hours, and calcined in air increasing the temperature to 600° C. over a period of about 4 hours, then maintaining the temperature at about 600° C. for 4 hours. After the calcination, the calcined catalyst was ground uniformly with a mortar and then shaped again into the pellet. The catalyst particles which have 250 to 500 µm particle size were selected with sieves.

A schematic diagram of the experimental setup for the catalytic activity test is shown in FIG. 3. Fuel was atomized by an ultrasonic-injector for delivery. The reactor was made of 12.7 mm stainless steel tubes placed inside electric furnaces. The reactor was controlled using PID temperature controllers and was monitored by thermocouples placed at the bottom of the catalytic bed. The fuel and de-ionized water (>15MΩ) was supplied by a high performance liquid chromatography (HPLC) pump (MOLEH Co. Ltd.). The water was supplied to a steam generator. A small quantity of nitrogen was also fed into the steam generator and ultrasonic injector to obtain a stable delivery of the reactants. The total flow of nitrogen was 120 ml/min, 20 ml/min for steam generator and 100 ml/min for ultrasonic injector nozzle. The air and nitrogen were metered using mass flow controllers (MKS Co. Ltd.). A gas chromatograph equipped with a Thermal Conductivity Detector (TCD) and a Flame Ionization Detector (FID), was used to analyze the compositions of the diesel reformate. It should be noted that the water component was removed by water trap before analyzing the compositions of the diesel reformate. Also, the temperatures of gas pipelines of the equipment were maintained above 150° C. with heat bands.

Example 1

Figure 4A:
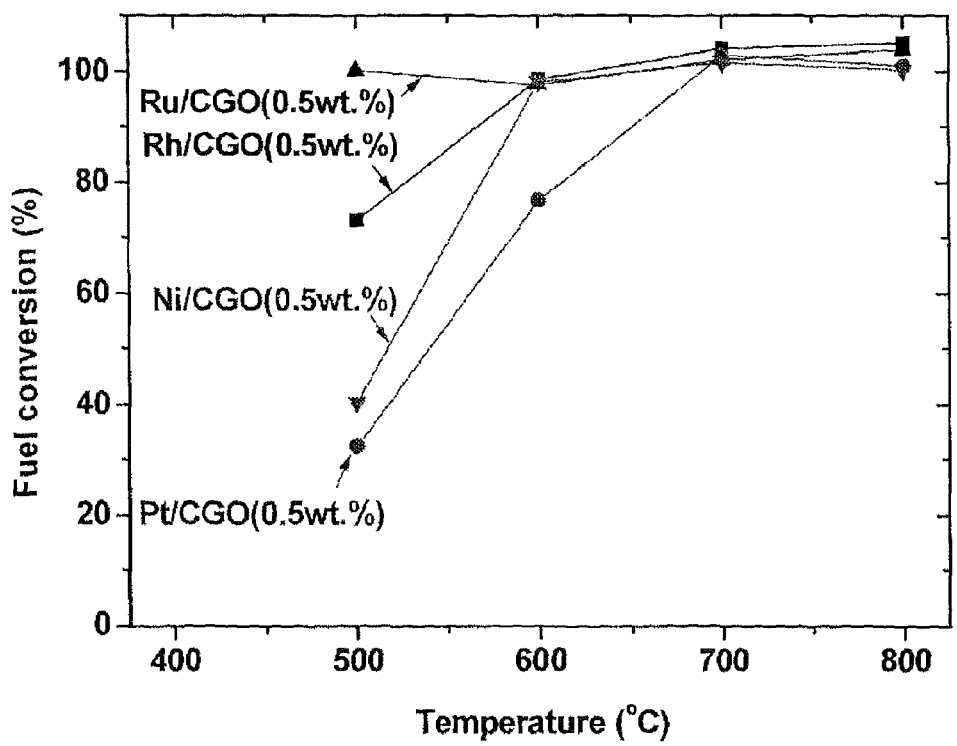
FIGS. 4(a) and (b) show fuel conversion and methane production over catalyst compositions.
Figure 4B:
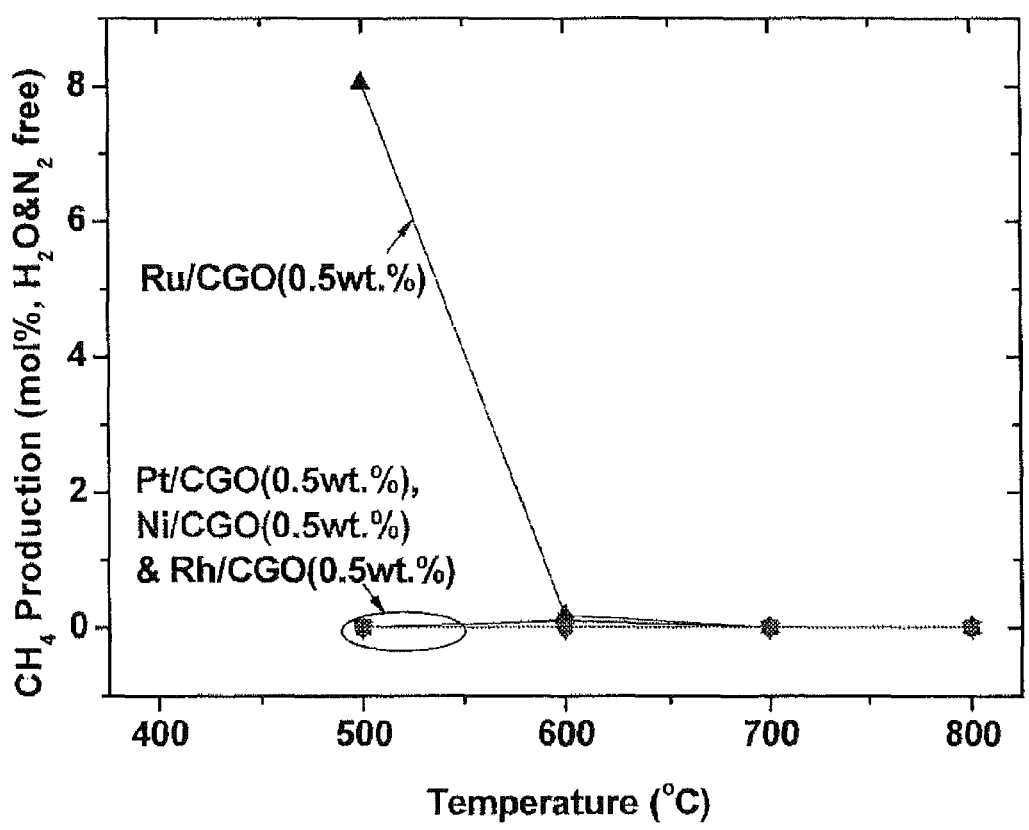
Figure 5:
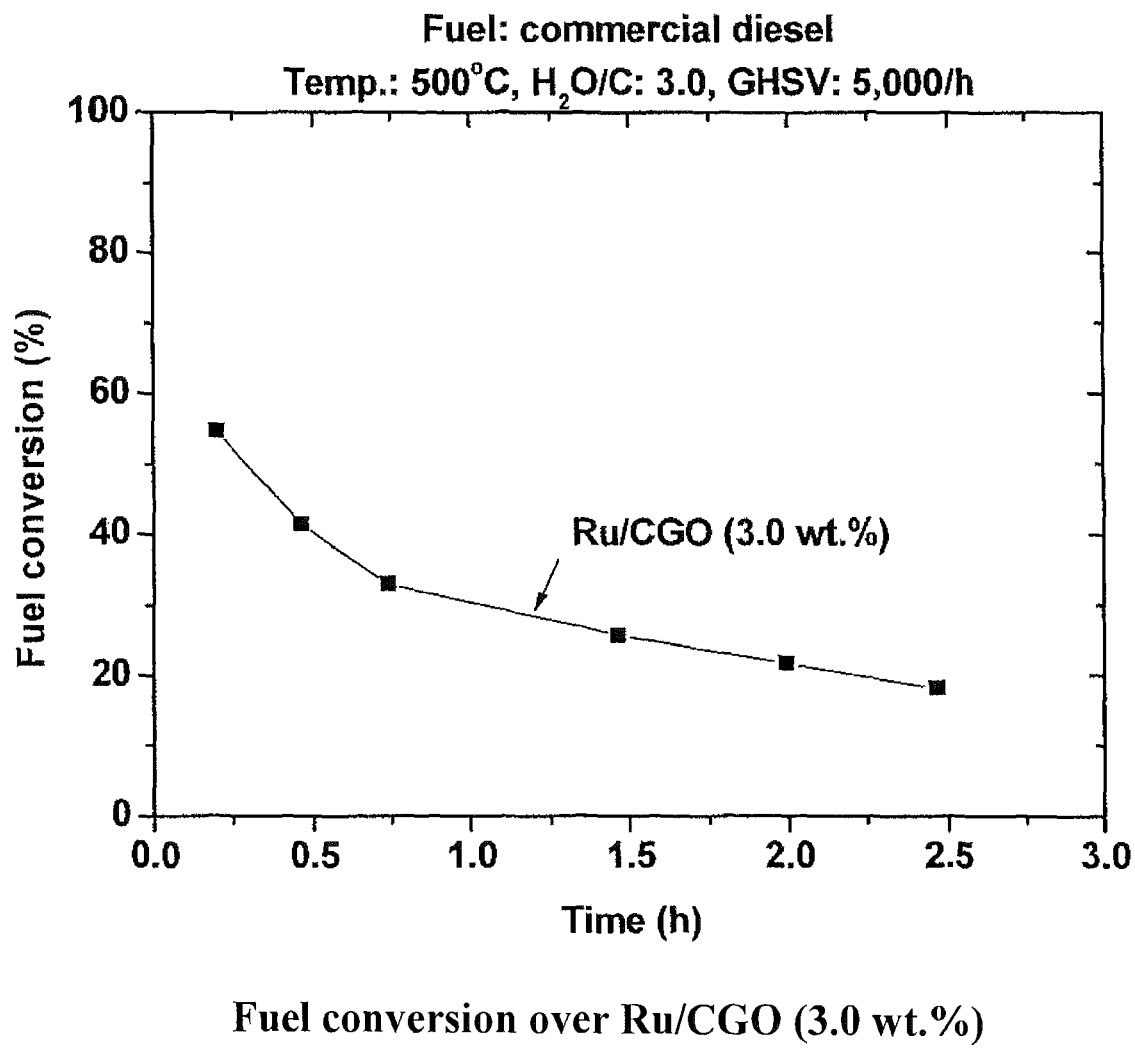
FIG. 5 shows fuel conversion over a catalyst composition.
Figure 6A:
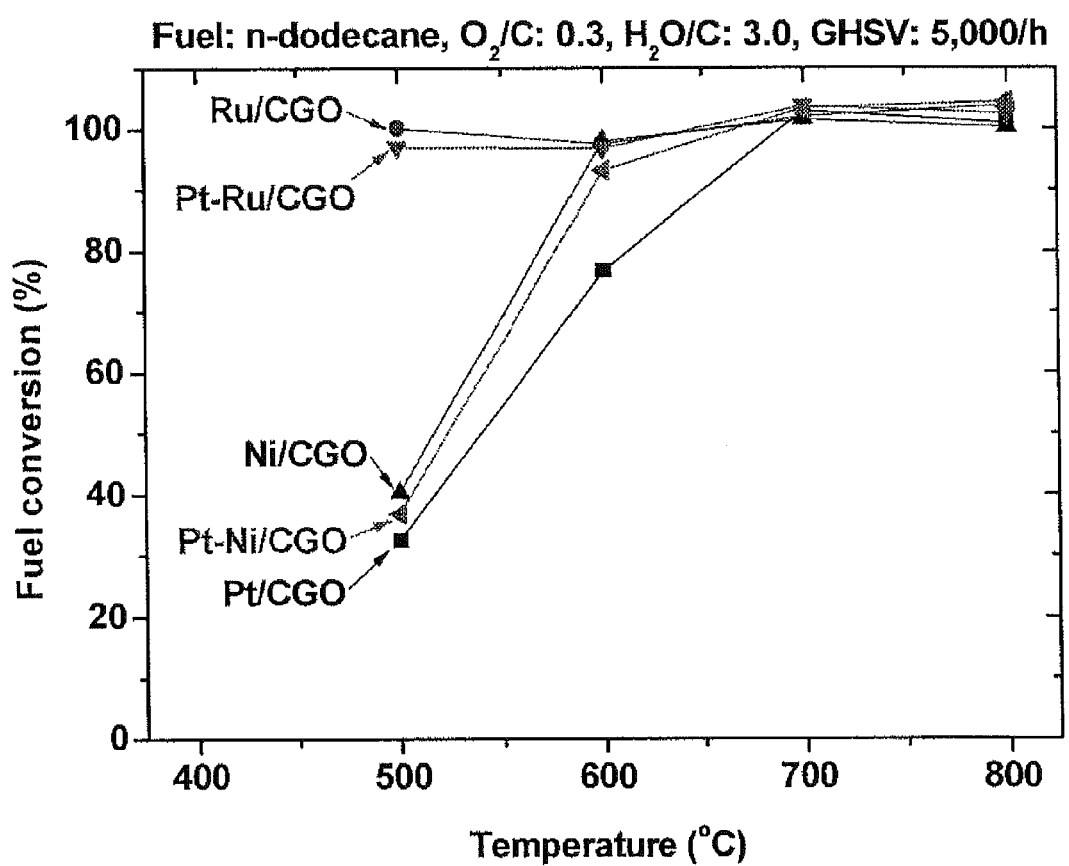
FIGS. 6(a) and (b) shows fuel conversion over catalyst compositions.
Figure 6B:
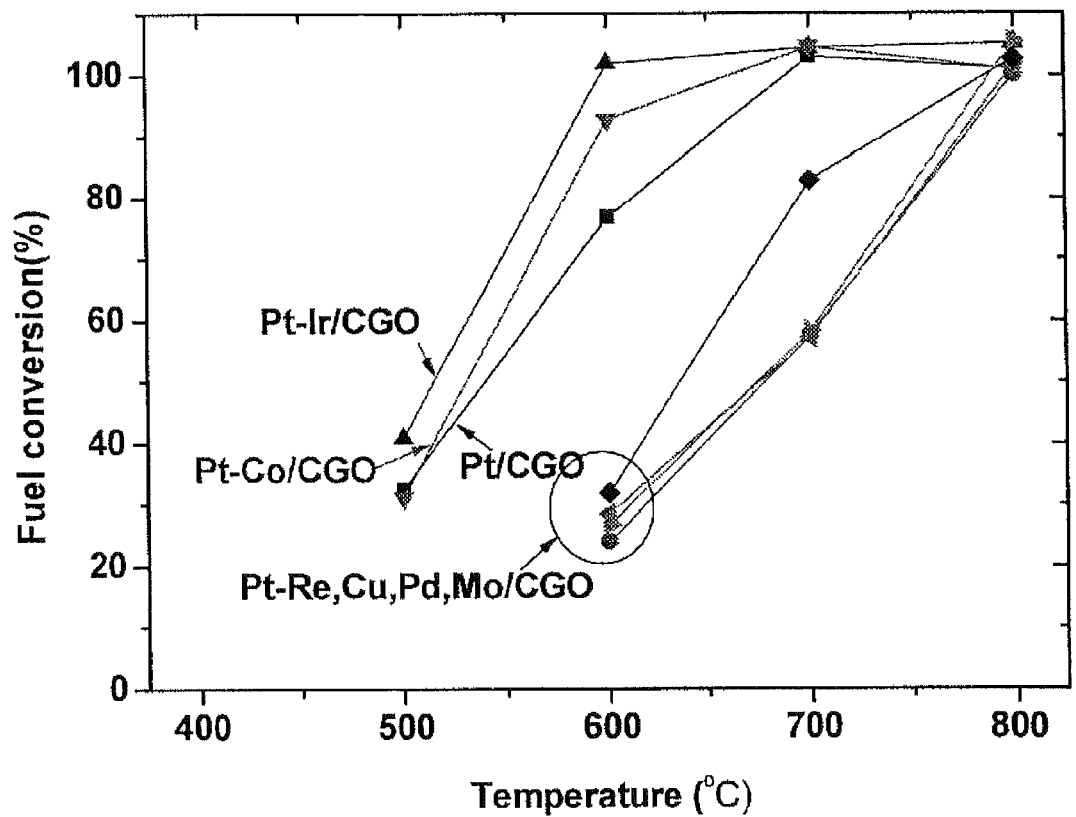

Pre-reforming using mono-metallic and bi-metallic catalysts was conducted. The results of case studies are follows:
1) Mono-Metallic Catalysts
Among mono-metallic catalysts, ruthenium/CGO showed the highest catalytic activity at 500° C. The results of pre-reforming over mono-metallic catalysts are shown in FIGS. 4(a) and 4(b). N-dodecane, ≥99% purity, anhydrous dodecane from Sigma-Aldrich Co., was used in this series of experiments. The pre-reforming of N-dodecane was conducted at an $O_2/C$ ratio of 0.3, a $H_2O/C$ ratio of 3.0 and a GHSV of 5,000/h. Ruthenium/CGO showed 100% fuel conversion and 8.0 mol % of methane production. However, Ru/CGO showed rapid degradation when pre-reforming was conducted using commercial diesel. Fuel conversion of commercial diesel pre-reforming over Ru/CGO is shown in FIG. 5. Less than 60% of the fuel was converted to syngas over Ru/CGO when commercial diesel was used.
2) Bi-Metallic Catalysts
No improvement of catalytic activity was observed over bi-metallic catalysts. Fuel conversion and methane production over bi-metallic catalysts are shown in FIGS. 6(a) and 6(b). In these experiments, N-dodecane was used. The pre-reforming was conducted at an $O_2/C$ ratio of 0.3, a $H_2O/C$ ratio of 3.0 and a GHSV of 5,000/h.

Example 2

Figure 7:
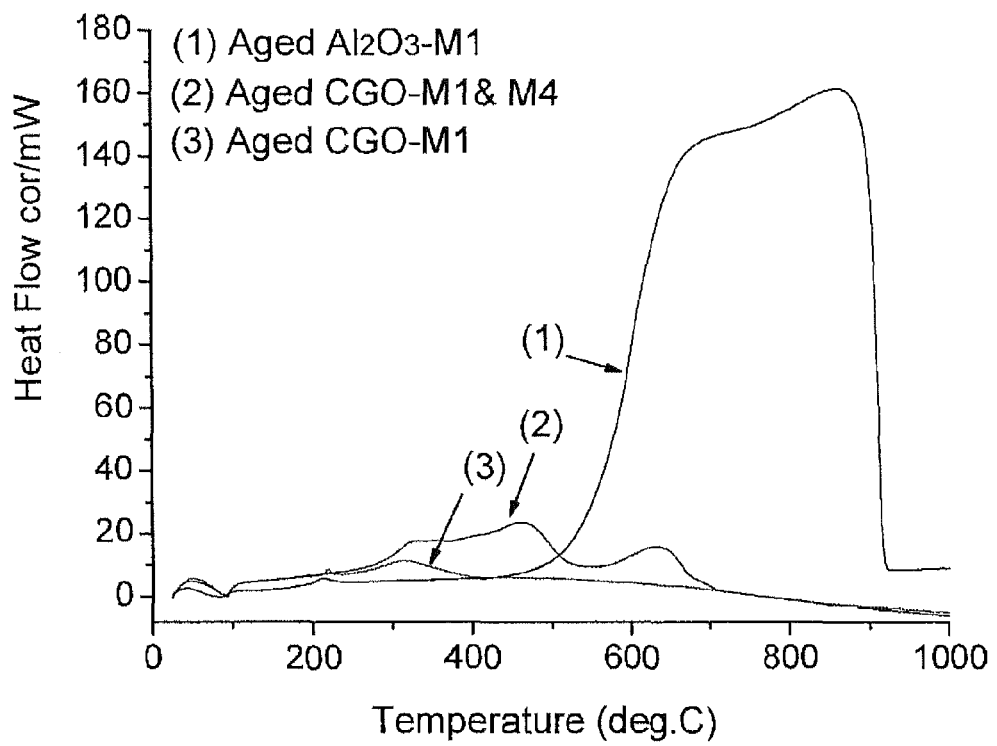
FIG. 7 shows the amount of coke formation over various catalyst compositions.

In reforming reactions, the redox cycle of CGO converts oxygen from of water and carbon monoxide into oxygen ions. The oxygen ions are diffused into the metal particles through the oxygen vacancy of CGO. The oxygen ion diffused to metal particles reacts with coke formed on nickel. Tests were conducted to analyze coke formation on CGO catalysts compared to commercially available catalysts. $Al_2O_3$ was obtained from Sigma-Aldrich. FIG. 7 shows the amounts of coke formation over CGO catalysts and $Al_2O_3$ after reforming tests. FIG. 7 shows Aged CGO-M1&M4 (M1 is platinum, and M4 is nickel) and Aged CGO-M1 (M1 is nickel). $Al_2O_3$ is widely used for catalyst supports, but is a nonionic conducting material. As shown in FIG. 7, coke formation is more significant on $Al_2O_3$ than CGO based catalyst compositions. In these tests, synthetic diesel was used. The synthetic diesel was a combination of N-dodecane (vol. 70%, ≥99% purity, Sigma-Aldrich) and 1-methylnaphthalene (vol. 30%, ≥99% purity, Sigma-Aldrich). The pre-reforming was conducted at an $O_2/C$ ratio of 0.5, a $H_2O/C$ ratio of 1.25 and a GHSV of 5,000/h.

Example 3

Generally, coke formation is a defect of nickel based catalyst compositions. Nickel is more prone to coke formation than other precious metal catalysts. In the present invention, the problem of coke formation on nickel based catalysts is alleviated by using CGO as supports.

Figure 8:
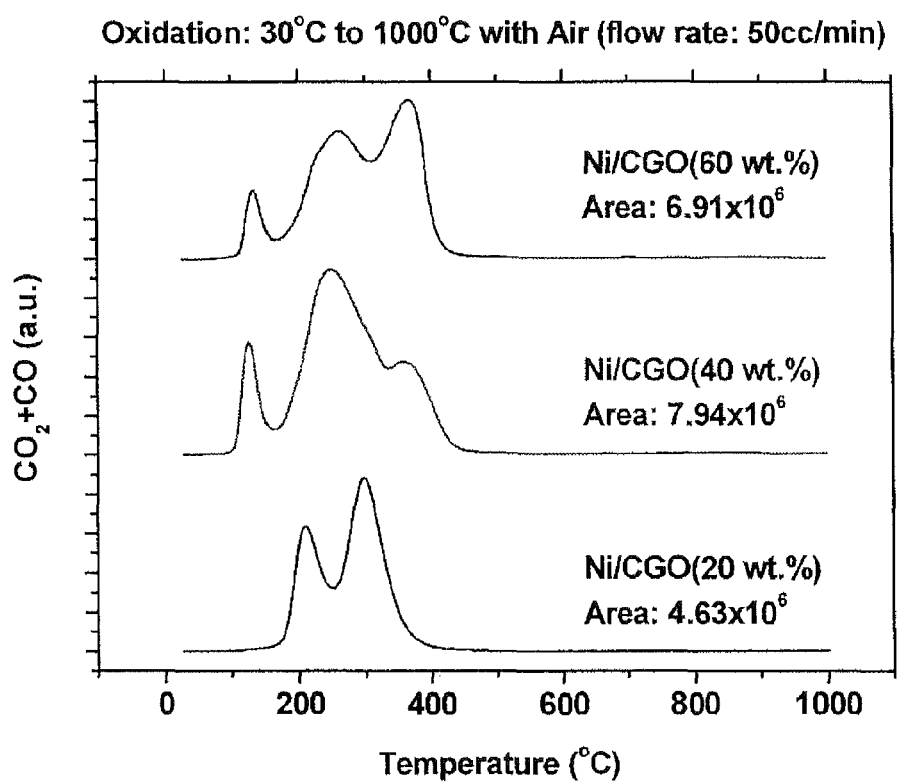
FIG. 8 shows the amount of coke formation over various catalyst compositions.

FIG. 8 shows the amount of coke formation after 10 hours of diesel pre-reforming over catalyst compositions with various nickel wt. %. Commercial diesel from GS-Caltex, South Korea was used for pre-reforming tests. The commercial diesel contains sulfur-containing compounds and aromatics. The pre-reforming was conducted at an $H_2O/C$ ratio of 2.0, a GHSV of 5,000/h, and a temperature of 500° C. As shown in FIG. 8, the catalyst with 20% nickel experienced the least amount of coke formation. In general, when the coke has a high temperature for burning it is hard to move by regeneration procedures because the burning temperature is related to the bonding energy of coke. In that respect, only catalyst compositions with 20 wt. % of Ni loading shows no coke is burned at 400° C.

Example 4

Figure 9:
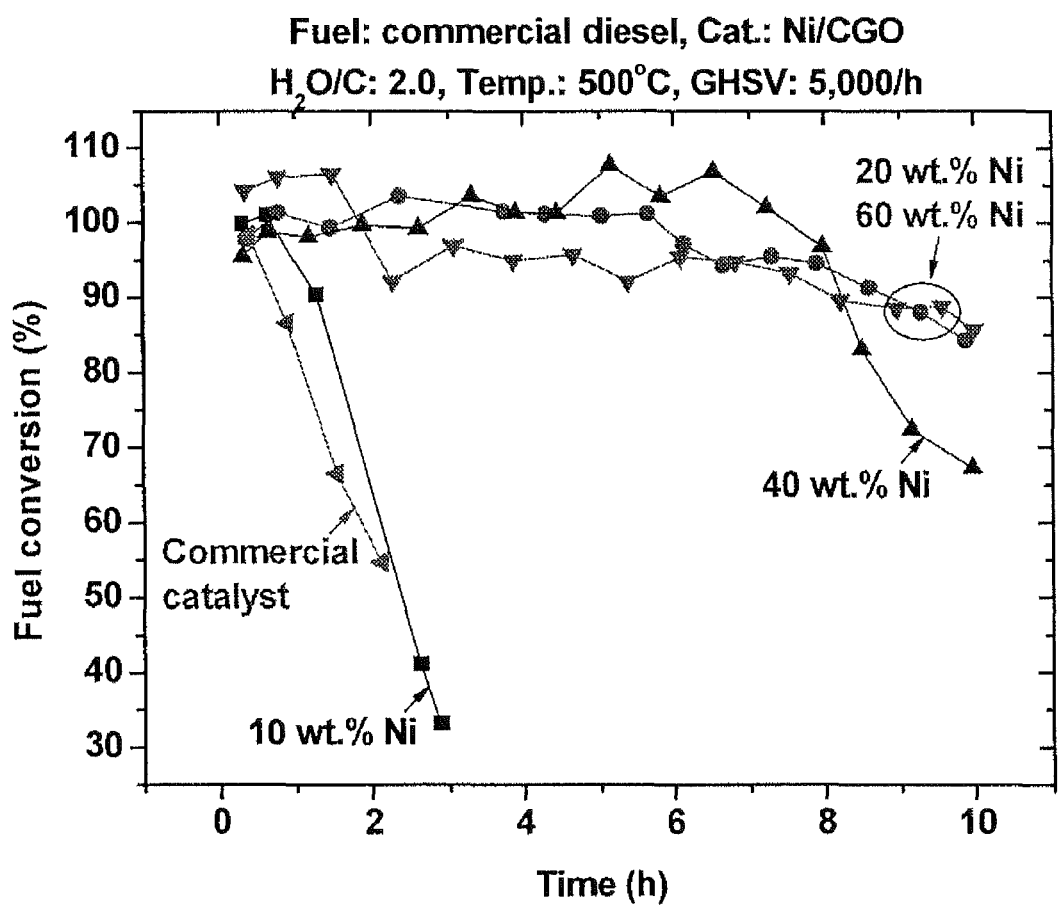
FIG. 9 shows the catalyst activity compared to nickel loading of several catalysts.

The activity and stability of catalysts depend on metal loading. A certain amount of metal loading is required to obtain enough catalytic activity for diesel pre-reforming. FIG. 9 shows the results of commercial diesel pre-reforming over various nickel loading of catalyst compositions. The pre-reforming was conducted at an $H_2O/C$ ratio of 2.0, a GHSV of 5,000/h, and a temperature of 500° C. When diesel pre-reforming was conducted over Ni/CGO (10 wt. %), fuel conversion decreases as shown in FIG. 9. Fuel conversion was greatly improved when nickel loading is higher than 20 wt. %. However, too high of metal loading decreases metal dispersion and interaction with supports and thus impacts the role that CGO plays in suppressing coke formation.

Example 5

Figure 10:
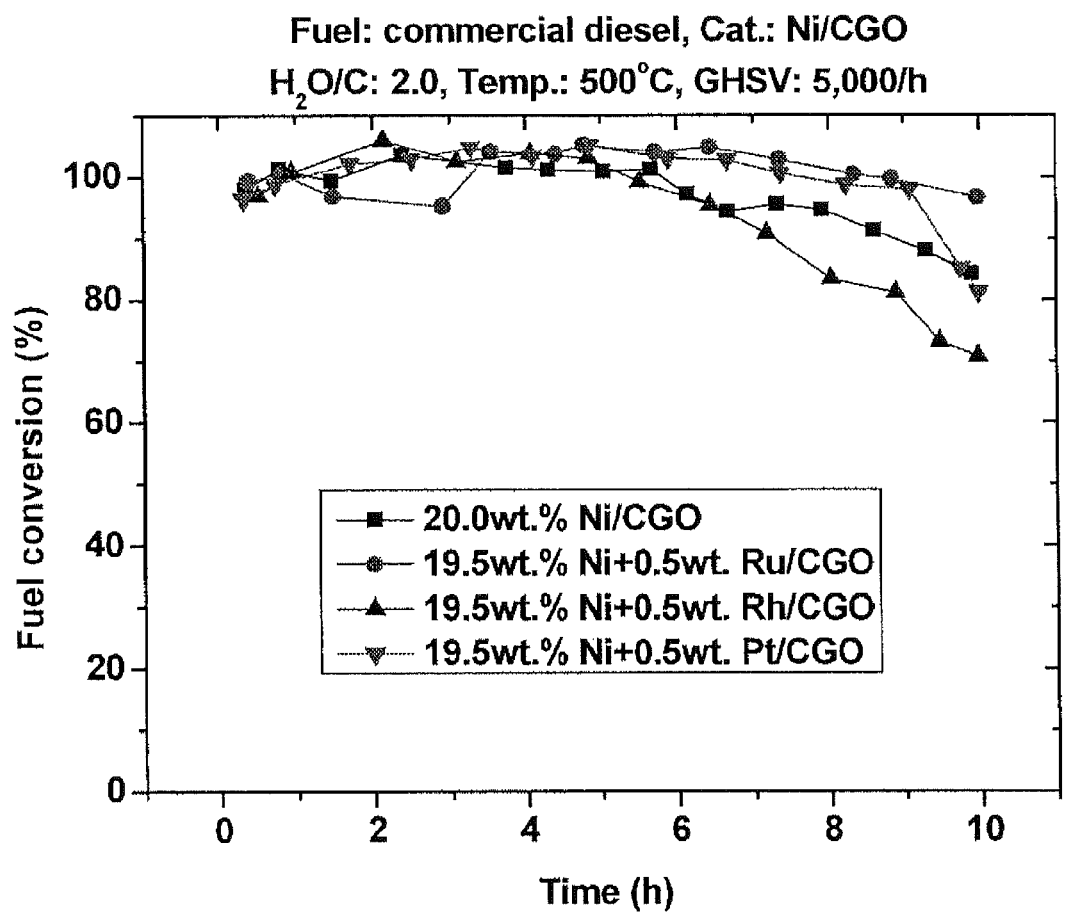
FIG. 10 shows the results of stability tests of nickel/CGO catalysts.

FIG. 10 shows stability of catalyst compositions with 0.5 wt. % of various precious metals, including ruthenium, rhodium, and platinum. FIG. 10 shows the results of commercial diesel pre-reforming over the catalysts for a period of 10 hours. The pre-reforming was conducted at an $H_2O/C$ ratio of 2.0, a GHSV of 5,000/h, and a temperature of 500° C. As shown in FIG. 10, the stability of the catalyst compositions was not improved by replacing 0.5 wt. % of nickel with rhodium or platinum. However, when 0.5 wt. % of Ni was replaced with ruthenium, the stability of the catalyst compositions was improved.

Figure 11:
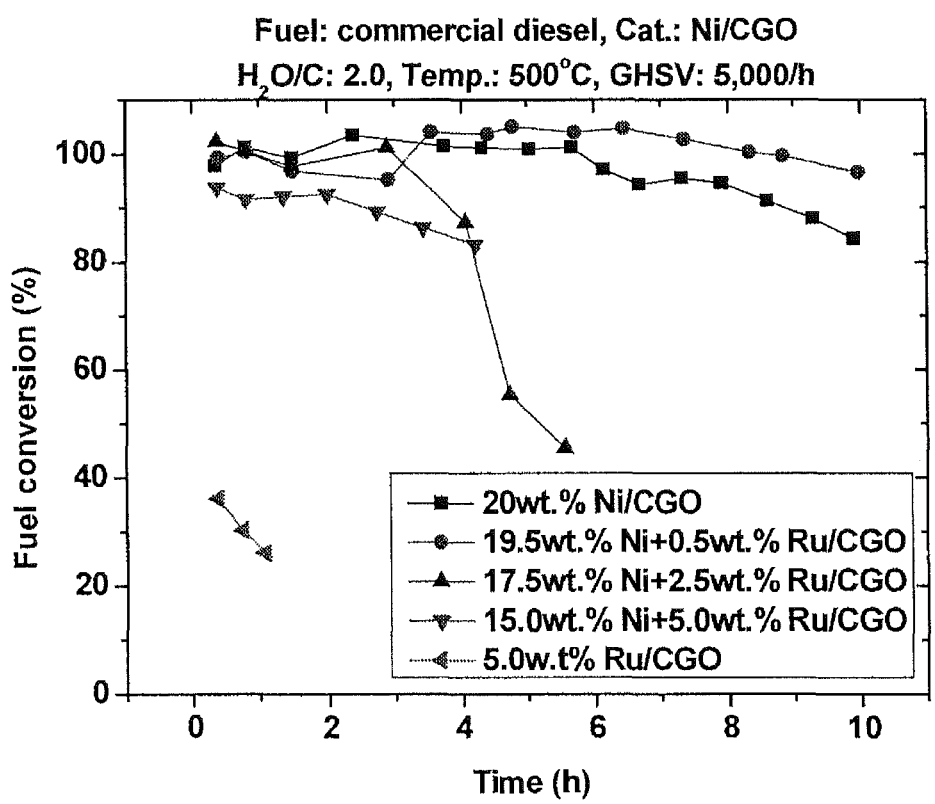
FIG. 11 shows the results of stability tests of nickel/CGO catalysts.

While ruthenium is effective to improve the stability of Ni/CGO, 0.5 wt. % was the optimized amount with respect to the amount of replacement. FIG. 11 is the result of stability tests illustrating 0.5 wt. % was the optimized amount for the replacement. FIG. 11 shows the results of commercial diesel pre-reforming over the catalysts for a period of 10 hours. The pre-reforming was conducted at an $H_2O/C$ ratio of 2.0, a GHSV of 5,000/h, and a temperature of 500° C. When the amount of replacement is greater than 0.5 wt. %, the improvement on stability is not obtained.

Example 6

Figure 12:
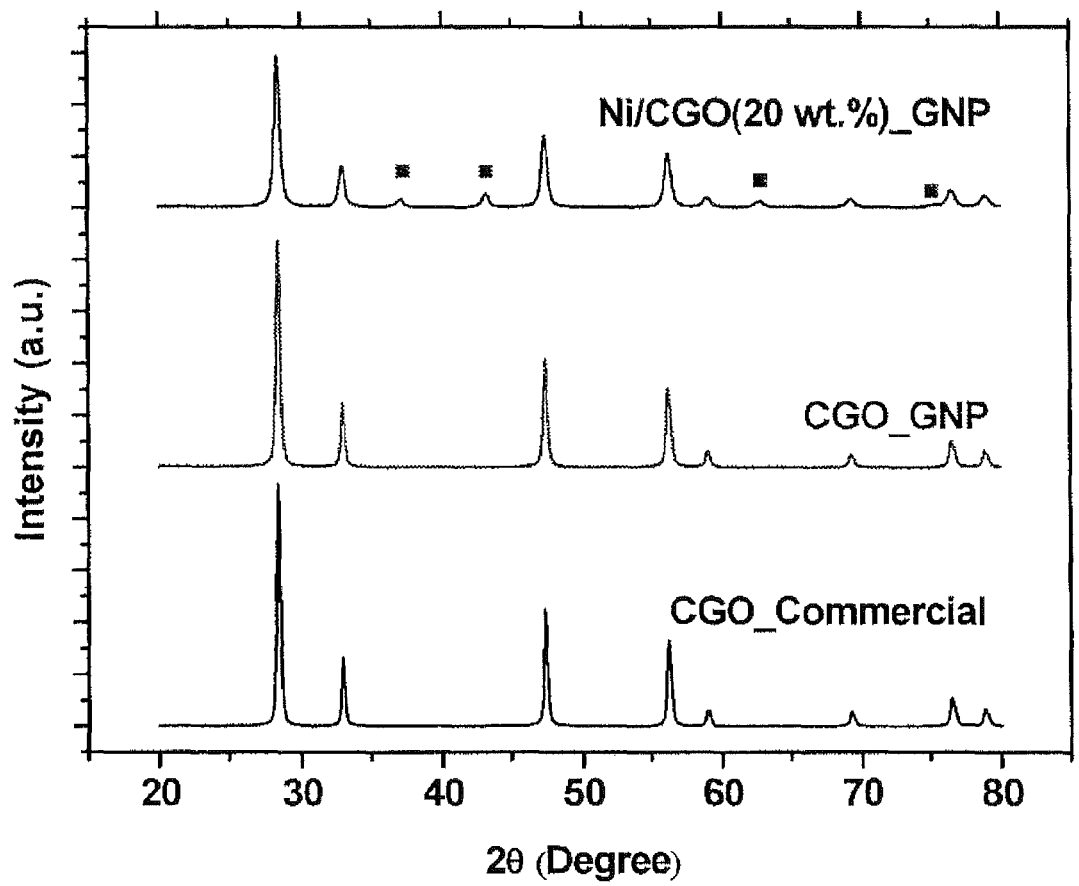
FIG. 12 shows XRD patterns of catalyst compositions.

Shown in FIG. 12 are XRD X-Ray Diffraction (XRD) patterns of nickel/CGO-CNP catalysts, CGO-GNP catalyst, and commercial CGO. When CGO was prepared by GNP according to the catalyst preparation method described above, the XRD pattern was consistent with commercial CGO. This indicated that the calcination process was proper to form the phase of CGO. Additionally, with the nickel/CGO-CNP catalyst, the CGO peaks was shown and additional peaks were identical to the peaks of nickel oxides.

Example 7

Figure 13:
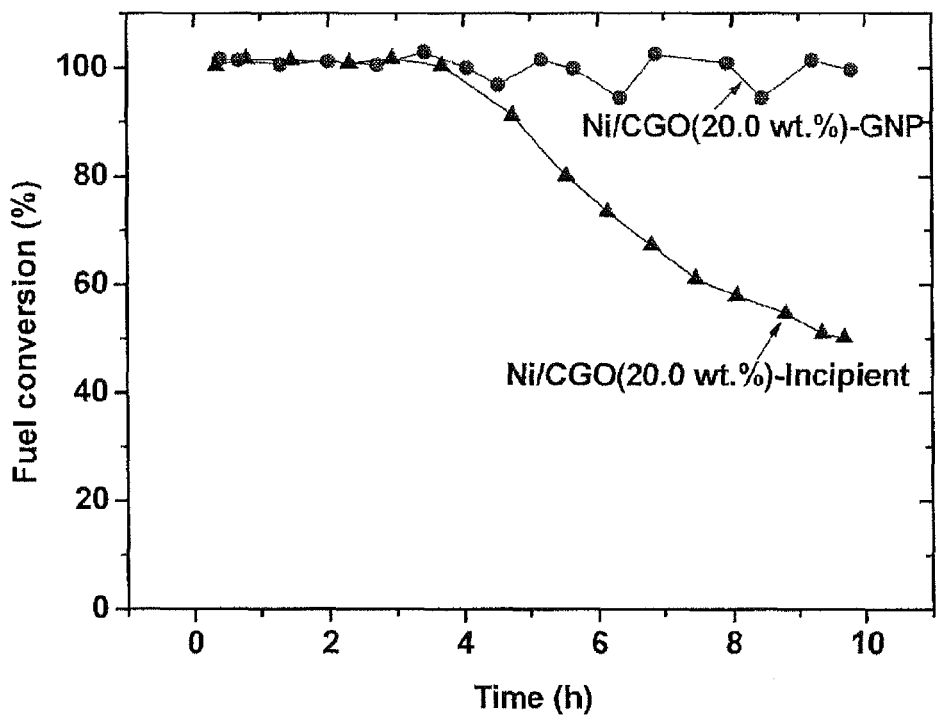
FIG. 13 shows fuel conversion over catalyst compositions.

FIG. 13 shows the results of commercial diesel pre-reforming over Ni/CGO (20.0 wt. %) prepared by GNP and incipient wetness impregnation (IWI). The pre-reforming was conducted at an $H_2O/C$ ratio of 3.0, a GHSV of 5,000/h; and a temperature of 500° C. Fuel conversion is the percentage of the number of carbon in product per the number of carbon in fed fuel. As shown in FIG. 13, commercial diesel was completely converted over both catalysts for the initial 4 hours. Ni/CGO (20.0 wt. %) prepared by IWI was degraded after 4 hours and only 50% of commercial diesel is converted at the end of the test. Ni/CGO (20.0 wt. %) prepared by GNP completely converts commercial diesel even after 10 hours.

Figure 14:
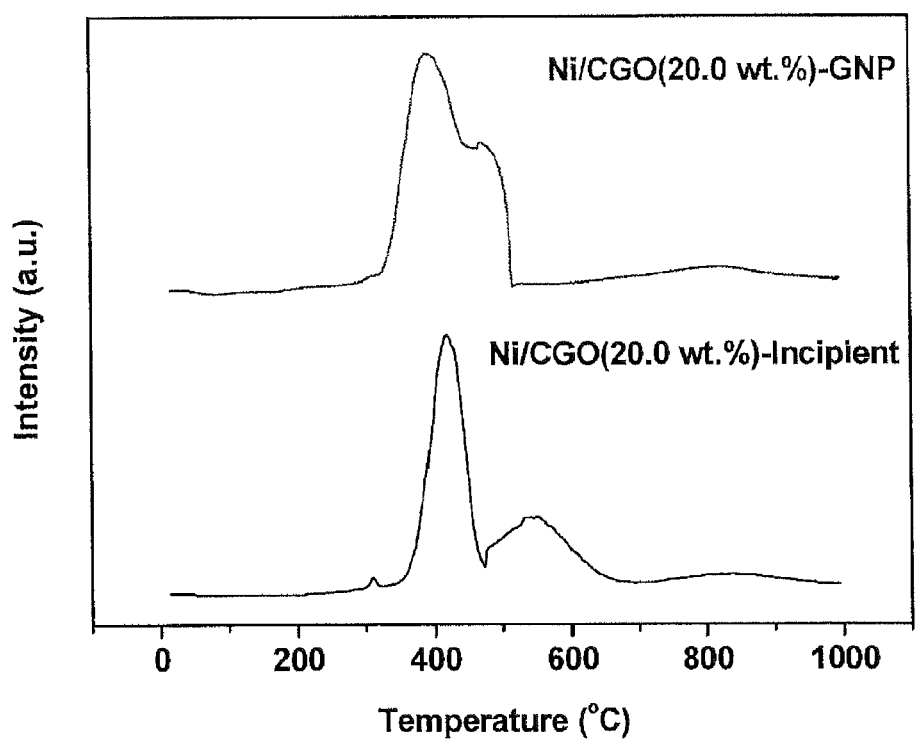
FIG. 14 shows TPR profiles of catalyst compositions.

FIG. 14 shows the Temperature Programmed Reduction (TPR) of Ni/CGO (20.0 wt. %) prepared by GNP and IWI. GNP reduced the reduction temperature of CGO. When Ni/CGO (20.0 wt. %) was prepared by GNP, CGO reduced at about 500° C. The reduction of CGO plays an important role in the ionic conduction for suppressing coke formation. The preparation method of the present invention thus improve the stability of the catalyst compositions by enhancing the reduction of CGO.

Example 8

Figure 15:
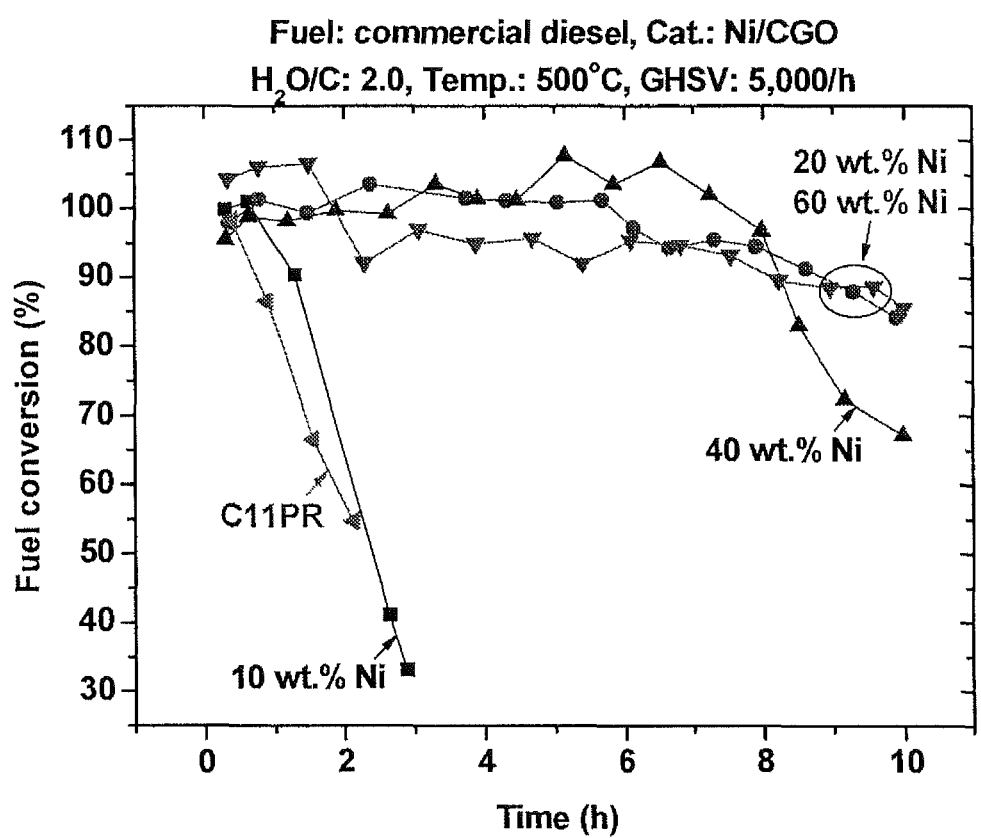
FIG. 15 shows accelerated degradation testing results of catalyst compositions.
Figure 16:
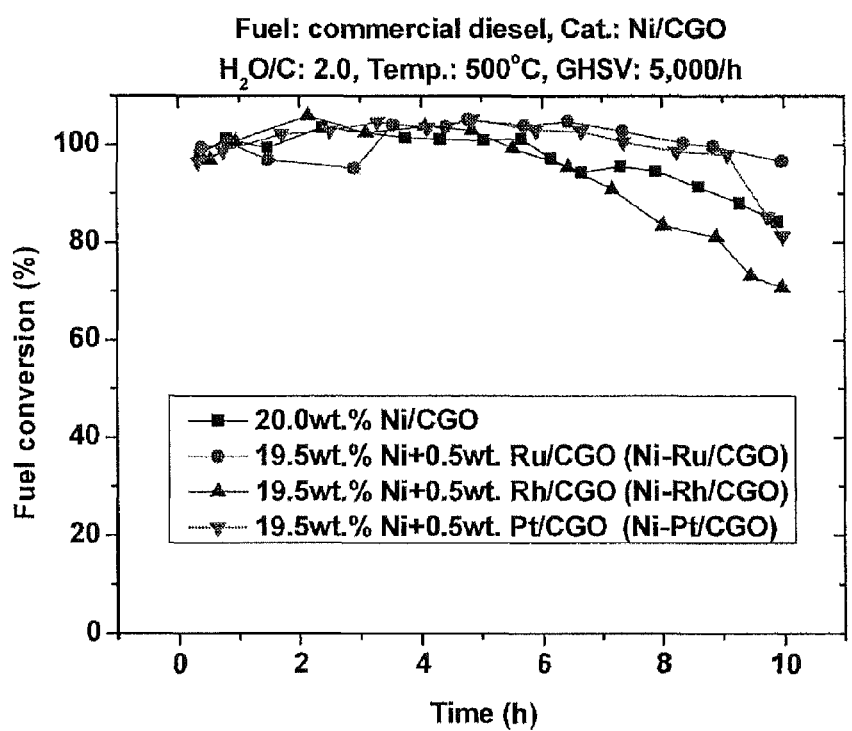
FIG. 16 shows accelerated degradation testing results of catalyst compositions.
Figure 17:
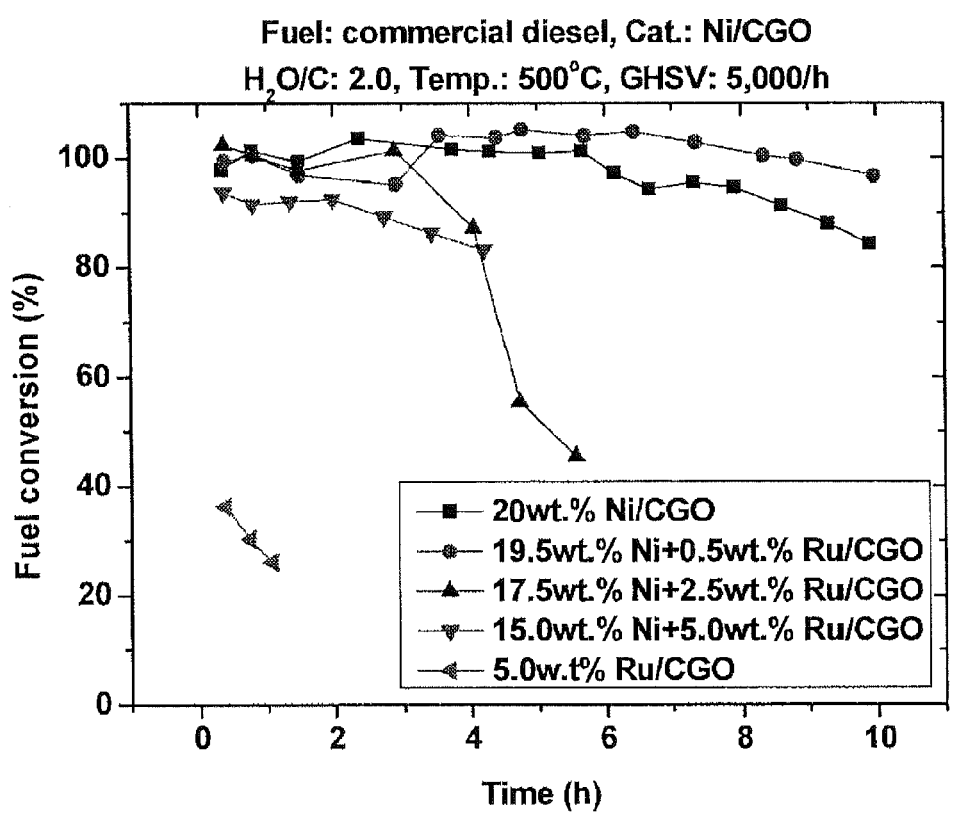
FIG. 17 shows accelerated degradation testing results of catalyst compositions.
Figure 18:
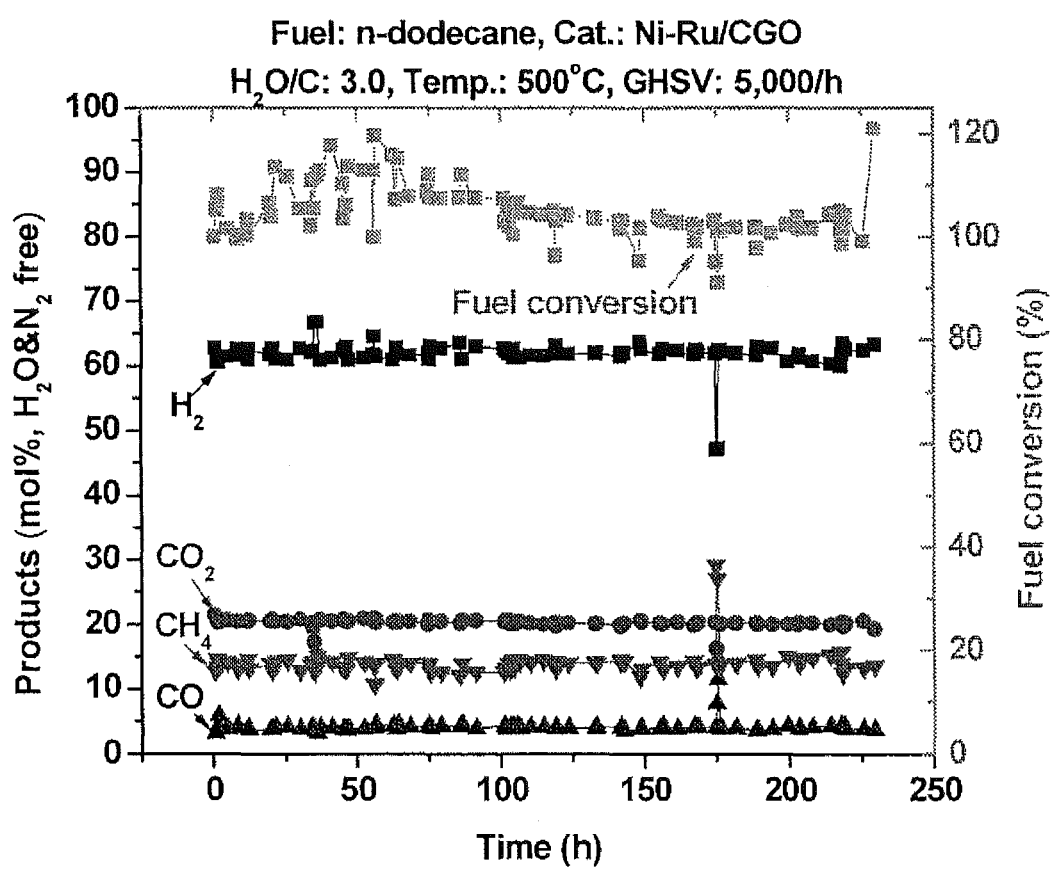
FIG. 18 shows the results of long term stability testing of catalyst compositions.

Ni/CGO based catalysts were optimized by case studies. The effects of nickel loading and precious metals on various catalyst compositions were investigated. The commercial diesel pre-reforming was conducted at a $H_2O/C$ ratio of 2.0, a GHSV of 5,000/h, and a temperature of 500° C. Low $H_2O/C$ of 2.0 was used to accelerate degradation. The results of nickel loading optimization are shown in FIG. 15. Although 20, 40 and 60 wt. % of nickel had similar stability, 20 wt. % showed lower coke formation than 60 wt. %. On the other hand, addition of ruthenium to Ni/CGO improved the stability as shown in FIG. 16. The optimized amount of ruthenium was 0.5 wt. %. More than 0.5 wt. % of ruthenium addition decreased the stability of Ni/CGO, as shown in FIG. 17. The optimized catalyst of Ni/CGO with 0.5 wt. % ruthenium was tested for long-term stability. For the long-term stability test, N-dodecane fuel was pre-reformed over the optimized catalyst at 3.0 of $H_2O/C$, 5,000/h of GHSV and 500° C. Gas chromatography (GC) results were obtained regularly, and molar ratio of each produced gas component and fuel conversion were calculated from the GC data. The optimized catalyst was stably operated for 200 hours, as shown in FIG. 18.

Example 9

The activity of Ni/CGO based catalysts stably was monitored for the amount of methane rich gas produced from commercial diesel fuel. Commercial diesel fuel was pre-reformed over 20% Nickel/CGO catalysts at 3.0 of $H_2O/C$, 5,000/h of GHSV and 500° C. The yield of methane gas was approximately 13% ($H_2O$ and N2 free) of methane rich gas.

That which is claimed is:

1. A catalyst comprising:
    a nickel component of about 20% wt.,
    a cerium oxide component of about 70% wt.,
    and gadolinium oxide component of about 10% wt.,
    wherein said catalyst converts diesel type liquid hydrocarbons to methane rich gas.

2. The catalyst of claim 1 wherein the catalyst is resistant to the formation of coke on the catalyst during use of the catalyst.

3. A method of activating the catalyst of claim 1 comprising:
    reducing the catalyst with hydrogen and nitrogen at about 500° C. for about 4 hours.

4. The method of claim 3 wherein the hydrogen is about 30% wt.

5. The method of claim 3 wherein the nitrogen is about 70% wt.

6. A method of regenerating the catalyst of claim 1 comprising:
    treating a catalyst of claim 1 that has been used for converting diesel type liquid hydrocarbons to methane rich gas with a treatment of water, hydrogen, and nitrogen at atmospheric pressure for a sufficient amount of time to remove coke formation on the catalyst.

7. The method of claim 6 wherein the hydrogen is about 30% wt.

8. The method of claim 6 wherein the nitrogen is about 45% wt.

9. The method of claim 6 wherein the water is about 45% wt.

10. A method of using the catalyst of claim 1 wherein diesel type liquid hydrocarbons are applied to the catalyst and a methane rich gas is produced.

11. The method of claim 10 wherein the diesel type liquid hydrocarbons are converted to methane rich gas at a rate of 90% or greater.

12. A catalyst comprising:
   a nickel component of about 19.5% wt.,
   a cerium oxide component of about 70% wt.,
   a gadolinium oxide component of about 10% wt., and
   a ruthenium component of about 0.5% wt.

13. A method of preparing a catalyst for converting diesel type liquid hydrocarbons to methane rich gas, said process comprising the steps of:
   adding stoichiometric amounts of $Ce(NO_3)_3 \cdot 6H_2O$, $Gd(NO_3)_3 \cdot 6H_2O$, and $Ni(NO_3)_3 \cdot 6H_2O$ to de-ionized water to create a dissolved solution;
   adding glycine to the dissolved solution to create a glycine-dissolved solution;
   heating the glycine-dissolved solution such that excess water is evaporated, combustion is initiated, and a catalyst powder is produced; and
   calcining the catalyst powder in air at about 800° C. for about 4 hours.

14. The method of claim 13 wherein the catalyst powder is shaped into a form for use in converting diesel type liquid hydrocarbons to methane rich gas.

15. The method of claim 13 wherein the form is catalyst pellets.

16. The method of claim 13 wherein the molar ratio of glycine to $NO_3$ of the glycine-dissolved solution is about 1.5.

17. The method of claim 13 wherein the catalyst powder has particles in the size range of about 10 nm to 20 nm.

18. The method of claim 13 wherein calcining the catalyst powder step comprises increasing the temperature to about 800° C. over a period of about 4 hours, and then maintaining the temperature at about 800° C. for 4 hours.

\* \* \* \* \*